United States Patent [19]

Chryssanthou

[11] 4,130,395
[45] Dec. 19, 1978

[54] PROCESS AND APPARATUS FOR DETECTION OF SPECIFIC BIOLOGICAL FACTORS BY MEANS OF OSMOTIC HEMOLYSIS

[75] Inventor: Chryssanthos P. Chryssanthou, Cliffside Park, N.J.

[73] Assignee: Beth Israel Medical Center, New York, N.Y.

[21] Appl. No.: 605,955

[22] Filed: Aug. 19, 1975

[51] Int. Cl.$^2$ ............................................. G01N 33/16
[52] U.S. Cl. ................................. 23/230 B; 195/127; 252/408; 424/11; 424/12; 422/67; 422/68
[58] Field of Search .................. 424/11, 12; 23/230 B, 23/253 R, 259; 252/408

[56] References Cited

U.S. PATENT DOCUMENTS

| B 544,476 | 2/1976 | Pinto | 23/230 B X |
|---|---|---|---|
| 3,617,222 | 11/1971 | Matte | 424/11 |
| 3,728,079 | 4/1973 | Moran | 23/259 X |
| 3,843,777 | 10/1974 | Hainski | 424/11 X |
| 3,899,298 | 8/1975 | Szczesniak | 23/230 B |
| 3,956,477 | 5/1976 | Price | 424/11 X |

Primary Examiner—Sidney Marantz
Attorney, Agent, or Firm—Blum, Moscovitz, Friedman & Kaplan

[57] ABSTRACT

The extent of lysis or red blood cells treated with a test solution containing a known or suspected agglutinating factor, and preferably with a lipid, serves for blood typing and cross matching, and, in addition for the detection and semi-quantitation of tumor factors and of viruses including myxoviruses (influenza, mumps) and adenoviruses (herpes), and of antibodies to such viruses. The method involves as one step the agglutination of erythrocytes (RBC) as well as lysis. Consequently, it is useful for detecting agglutinating factors. An apparatus for carrying out the method automatically is described.

44 Claims, 4 Drawing Figures

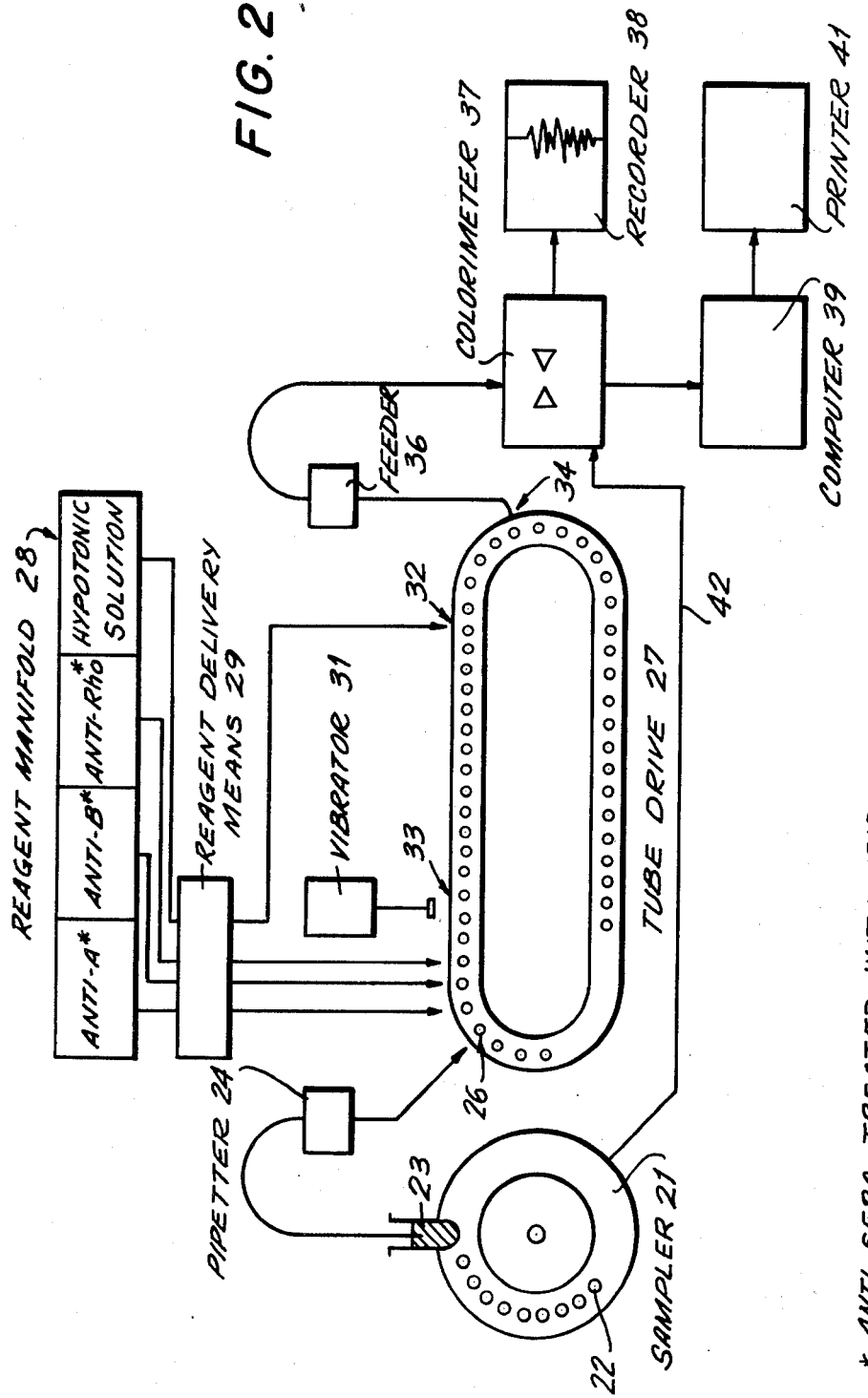

PROCESS AND APPARATUS FOR DETECTION OF SPECIFIC BIOLOGICAL FACTORS BY MEANS OF OSMOTIC HEMOLYSIS

BACKGROUND OF THE INVENTION

With the increase in cost of laboratory tests, and with the proliferation of useful tests as the knowledge of pathology and physiology in general and of immunology and blood-banking in particular, increases, it becomes most desirable to develop test procedures which can be carried out quickly, precisely, in large numbers and, wherever possible, automatically. Typing of blood is particularly important from the above standpoints due to the fact that it is one of the tests most frequently carried out. It is done essentially on a routine basis whenever a patient enters a hospital for surgery due to the fact that transfusion of blood may become necessary. It is extremely important to determine whether a pregnant woman may be Rh negative and the father Rh positive. Problems also arise where an individual who is Rh negative receives a transfusion of Rh positive blood. A second transfusion of blood of this type to such an individual can develop a severe reaction.

Where it is suspected that a patient is suffering the effects of infection with a specific virus, a rapid, simple and reliable test for determing whether the patient has been infected with said specific virus would be of substantial value. The value of such a test would be increased if the test could be carried out automatically. It would be desirable in this respect to be able to test for the presence of an antibody to the specific virus in the blood of the individual.

SUMMARY OF THE INVENTION

As is well-known, red blood cells, henceforth to be termed RBC, undergo osmotic hemolysis when placed in water or in a hypotonic solution, as a result of which the solution turns red. Furthermore, RBC, when brought in contact with a serum or test solution, the term "test solution" as used herein including dispersions as well, said serum or test solution containing an agglutinating factor which is specific to the RBC type, are agglutinated thereby. Applicant has found that clumped cells, when placed in water or in hypotonic solution also undergo osmotic hemolysis but to a substantially lesser extent. More importantly, however, applicant has also found that the degree of osmotic hemolysis is greatly reduced if the clumped cells are treated with a lipid, directly or indirectly, prior to bringing same in contact with the hypotonic solution, water, of course, also being a hypotonic solution. The term lipid as used herein denotes hydrophobic substances of which oils and fats are examples. Further, if the serum or test solution containing an agglutinating factor specific to the RBC is treated with a lipid prior to bringing the serum or test solution into contact with the RBC, then, once more, the degree of hemolysis is greatly reduced. By these means either unknown RBC or an unknown serum can be typed. Unknown RBC can be typed by the use of sera of known type, and an unknown serum can be typed by the use of RBC of known types. The method is applicable to distinguishing RBC and sera as to types A, B, AB and O. In addition, it is applicable to typing with respect to the Rh and Coomb's factors and with respect to M and N factors.

The method of the present invention is further applicable to the detection of viruses which agglutinate RBC. To carry out such a detection procedure, such a procedure also being amenable to semi-quantitation of antibodies, serum from the patient is mixed with a solution known to contain the suspected virus. Following treatment of this solution with a lipid, the lipid-treated solution is brought in contact with RBC. If the patient is infected with the suspected virus, there will be corresponding antibodies in his blood. These antibodies when mixed with the test solution containing the suspected virus will complex with the virus so that the virus cannot combine with the RBC. Consequently, the degree of lysis will be greater than will be the case where the lipid-treated virus solution is mixed with a serum containing no antibodies and is then brought in contact with RBC and placed in hypotonic solution. Certain tumor components appear to be agglutinating factors or to contain agglutinating factors. These components may be extracted and tests carried out on the extract in a manner similar to that used for detecting the presence of a specific virus.

As aforenoted, sera can also be typed using RBC of known types and noting the degree of lysis for various combinations when when placed in hypotonic solution. Preferably the serum is first brought into contact with a lipid, after which the lipid-treated serum is brought into contact with RBC of known types. Finally, the so-treated RBC are brought into contact with hypotonic solution and the degree of lysis noted.

Some lysis takes place under all conditions specified above. Consequently, it is necessary that the various steps of the method be carried out under standardized conditions. Room temperature has been found to be suitable. In addition, a test solution is treated with lipid by shaking for a specific length of time, after which the lipid is separated off. Similarly, lipid-treated serum is shaken with RBC for a specific length of time, after which the composition is allowed to incubate for a standardized period. Finally, so far as lysis of the RBC is concerned, the RBC are held in contact with the hypotonic solution for a specific length of time and then allowed to stand for a standardized period before measuring the degree of lysis colorimetrically.

A variety of lipids have been found to be useful, the edible oils and fats and petroleum oil giving satisfactory results. Peanut oil and corn oil have been found to give the greatest degree of contrast in the extent of lysis as against controls. Where fats are used, they are liquified by raising the temperature.

In preparation for carrying out the present method automatically, red blood cells, either of known types or of unknown type as when taken from a patient or donor must be obtained by conventional means including the withdrawal of blood samples, separation of RBC from serum by centrifugation, washing of the RBC with normal saline and suspending the RBC in normal saline. Specimens of RBC, in one embodiment of the invention, are supplied to three test tubes, to each of which are also supplied one of anti-A, anti-B and anti-Rho sera, each of the sera having been treated with a hydrophobic substance, and separated therefrom. After shaking and incubating as aforenoted, the serum-treated RBC are brought in contact with a hypotonic solution under standardized conditions to hemolyse. The three hemolysates are transferred automatically to cuvettes, which are then inserted into a colorimeter. Using a light beam and a photodetector, the optical density of the hemolysates is read. The optical density may be recorded or may be supplied to a computer which correlates the color intensity with the degree of hemolysis and decides whether the degree of hemolysis in each of the three tests is high or low as compared to controls. From these results the RBC can be typed as to A and B and Rh factors. The information is then sent to a printout or other display.

By means of obvious modifications of the above procedure, an unknown serum can be typed, and the nature and quantity present of a virus can be determined as can be the presence of antibodies in the serum of a patient. A similar procedure makes it possible to determine the presence of an agglutinating factor or factors from a tumor.

In another embodiment of the method in accordance with the present invention, the RBC, after treatment with a solution or serum containing or suspected of containing an agglutinating factor, are dropped into a test tube optionally having a lipid layer at the top thereof, a fixative solution at the bottom thereof and an intermediate layer of hypotonic solution. Such lysis as occurs takes place during the time required for the RBC to pass through the hypotonic solution layer by gravity. Again, by testing the RBC against enough types of sera, the RBC can be typed as to A and B factors and as to Rh factor and, in addition as to Coomb's and M and N factors. Also, as above, information with respect to tumor factors, viruses and antibodies can be obtained, and sera can be typed and bloods can be cross-matched. This embodiment can also be carried out automatically.

Accordingly, an object of the present invention is a method of detecting, both qualitatively and semi-quantitatively, an agglutinating factor in a serum or other solution.

Another object of the present invention is a method of typing blood automatically.

A further object of the present invention is a method of determining the presence of specific antibodies in serum.

An important object of the present invention is a method of typing red blood cells with respect to type-A and type-B factors as well as Rh factors, Coomb's factor and M and N factors.

A significant object of the present invention is an apparatus for typing blood and determination of agglutinating factors in serum and other solutions where said typing and determination are carried out automatically.

A valuable object of the present invention is a method and apparatus for determination of agglutinating factors depending on the extent of hemolysis of red blood cells in hypotonic solution.

Yet another significant object of the present invention is the detection of agglutinating factors in the extracts from various types of tumors.

Still other objects and advantages of the invention will in part be obvious and will in part be apparent from the specification.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 2 is a first embodiment of the apparatus in accordance with the present invention.

DESCRIPTION OF THE PREFERRED EMBODIMENTS

Figure 1A:
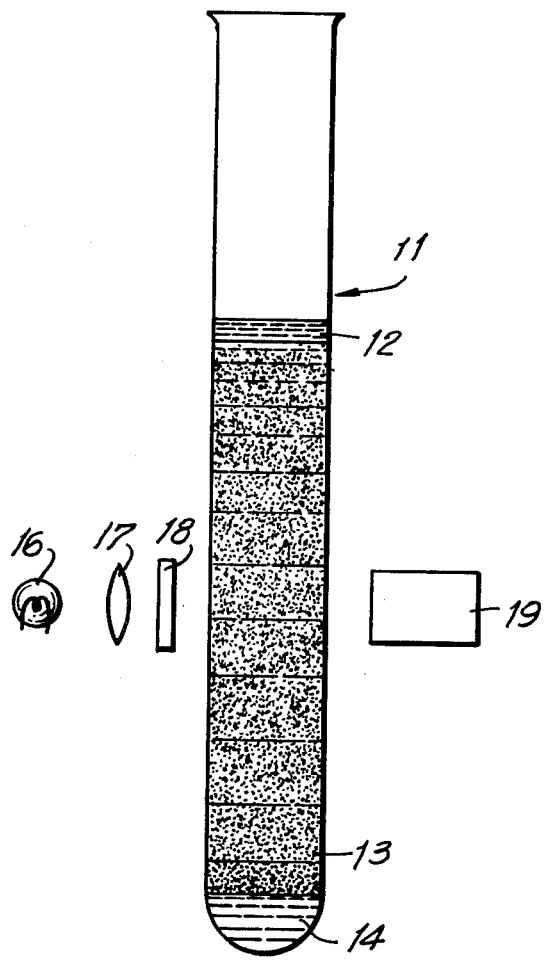
FIGS. 1a and 1b illustrate a method of carrying out hemolysis of RBC in accordance with the present invention wherein RBC which have been treated with a solution suspected of containing an agglutinating factor are passed by gravity successively through a lipid layer, a body of hypotonic solution and into a formalin solution in which the RBC are fixed.

The present invention concerns a new method and related devices based on the extent of hemolysis of treated RBC when brought in contact with a hypotonic solution.

The method and the related devices are useful for:
1. The identification and differentiation of various types of RBC;
2. The identification and differentiation of various types of sera; and
3. The detection of semi-quantitation of substances which:
   3.1 agglutinate erythrocytes (RBC);
   3.2 attach to RBC;
   3.3 can be processed so that they attach to RBC; and
   3.4 can prevent other substances from agglutinating RBC or from attaching to RBC.

The method may be used for, but is not limited to, blood-typing, cross-matching, detection or semi-quantitation of viruses including myxoviruses (influenza, mumps) and adenoviruses (herpes) and of antibodies to such viruses. The method of the present invention is based on applicant's observation that osmotic lysis of RBC induced by hypotonic solution, the term hypotonic solution also including water as well as solutions of solids, and consequent release of hemoglobin is prevented, reduced or delayed when RBC are interacted with a "detachable factor", also termed an "agglutinating factor", and with a hydrophobic substance such as a lipid prior to contact of said RBC with said hypotonic solution. Such changes in the rate of hemolysis and in the amount of hemoglobin released provide a convenient and measurable end point for the qualitative and, under certain circumstances, for the semi-quantitative determination of the agglutinating factor. This phenomenon is not related to and is clearly differentiated from "immune hemolysis" which refers to lysis of RBC resulting from interactions between RBC - membrane antigens, specific antibodies against those antigens and hemolytic complement. It can also be differentiated from any lysis of RBC produced by a variety of chemical or biological agents (e.g., drug-induced lysis). The basic difference is that in contrast to all other hemolytic processes, the lysis of RBC in accordance with the present invention is always produced by osmotic influx of water into the RBC after placing in hypotonic solution.

The basic principle of the method of the present invention is illustrated by the following example Human type-A RBC when brought in contact with a hypotonic solution lyse almost immediately and their hemoglobin is released as expected, the release being readily notable by the increase in color. When, however, these type-A RBC are interacted with anti-A agglutinin and then introduced into a column of hypotonic solution at the top thereof, the RBC will lyse at a somewhat lower rate than would RBC not treated with anti-A agglutinin. The difference in the rate of lysis serves for blood-typing and identifying various agglutinating agents.

In a preferred form of the test, human type-A RBC are interacted with anti-A agglutinin and then deposited into a layer of a fatty substance such as peanut oil which is overlying a column of water or hypotonic solution; the RBC lyse only slightly when they pass by gravity from the layer of fatty substance into the hypotonic solution. For convenience, the fatty substance will be referred to generally as a lipid, although it is to be understood that hydrophobic substances in general are effective for the purposes. For instance, mineral oil is also relatively effective in preventing lysis under the conditions described.

As aforenoted, some release of hemoglobin occurs when the RBC which have been treated both with an agglutinating factor and a lipid are brought in contact with the hypotonic solution, but the amount of the released hemoglobin in smaller and the rate of release is much slower than from untreated RBC. Interaction of RBC with the lipid alone does not suffice to offer "protection" against osmotic hemolysis. Interaction of RBC with the corresponding agglutinin alone reduces only slightly the degree of osmotic hemolysis. It is therefore apparent that both factors (interaction with a corresponding agglutinin as well as with a lipid) are required for maximal "protection" against osmotic hemolysis.

A very important point is that the agglutinin, to be effective, must correspond to the RBC (e.g., anti-A agglutinin for type-A RBC). If the RBC are exposed to a non-corresponding agglutinin, that is, if type-A RBC are mixed with anti-B agglutinin, and then placed in the lipid phase, lysis will occur when the RBC reach the hypotonic phase. It is this specificity of the interacting components which permits detection either of the type of RBC or the type of agglutinin in the unknown material. The hypotonic solution which provides the greatest degree of contrast between protected and unprotected RBC is about 0.3% NaCl solution. Passage through a lipid phase, however, greatly increases the resistance of RBC to hemolysis.

The phenomenon desribed in the above examples (virtually absolute or relative protection against release of hemoglobin when RBC come in contact with $H_2O$) occurs with a variety of complexes between RBC and substances which attach to them. These complexes include RBC-phytohemagglutinin, type-A RBC-anti-A agglutinin, type-B RBC-anti-B agglutinin, Rh positive RBC-anti-Rh serum, Coomb's positive RBC - Coomb's serum (anti-human γ-globulin), RBC - influenza virus, etc. In the above-mentioned complexes the components bind to each other normally. By specific treatment, however, it is possible to produced complexes of RBC with substances which normally do not attach to RBC.

The mechanism whereby osmotic hemolysis and release of hemoglobin is prevented or delayed following interaction of RBC with a substance which attaches to them and with a lipid, is obscure. Following are possible explanations of the observed phenomena, it being noted that applicant's invention is not predicated on any specific theory. The lipid may bind to the agglutinating factor: (e.g. an isoagglutinin corresponding to the RBC) which in turn is attached to the surfce of RBC. Thus the lipid indirectly attached to the RBC may form a hydrophobic layer which protects the cell against influx of $H_2O$ and therefore against lysis. Or, the interaction of the agglutinating factor with elements of the surface of the RBC may cause surface changes which permit attachment of the lipid to the RBC with a resultant decrease in membrane permeability to $H_2O$. Consistent with the first hypothesis is the observation that if the agglutinating factor (e.g. isoagglutinin corresponding to the RBC) is passed through a layer of oil and then mixed with RBC, the RBC, when placed in $H_2O$, lyse at a slower rate than RBC mixed with a non-oil-treated agglutinating factor. If, however, the agglutinating factor after passing through a column of lipid is treated with ethyl ether in a separatory funnel (in order to remove the lipid) and then mixed with RBC, it gives a much smaller reduction in the rate of RBC lysis when the mixture is placed in $H_2O$. It is for this reason that the lipid may be more generally referred to as a hydrophobic substance or an oil.

From the foregoing it is apparent that the basic principle described can be applied to methods for the detection or semi-quantitation of agglutinating factors. The method essentially consists of a comparison of the amounts of liberated hemoglobin between a control mixture and a mixture which contains the test material. A smaller amount of released hemoglobin from the latter mixture will indicate the presence of an agglutinating factor in the test material. Serial dilutions of the test material and observation of the lowest concentration that results in protection against osmotic hemolysis provides means for semi-quantitation. The same principle can be used for the detection or semi-quantitation of substances which prevent other substances from attaching to, or from agglutinating RBC. For example, certain viruses, such as influenza virus, agglutinate or attach to RBC. The clumped RBC will lyse at a lower rate than untreated cells. When the virus or the RBC-virus complex is treated with oil, the RBC in the RBC-virus mixture either lyse only slightly or are strongly retarded in so doing when placed in a hypotonic solution. If, however, the virus is first reacted with a test material which contains antibodies against the virus, a virus-antibody complex is formed and the virus is no longer available to form the bridge for the attachment of lipid to the RBC and thus to protect the RBC against lysis. In this case lysis of RBC will indicate the presence of a viral antibody in the test material whereas absence, diminution or retardation of lysis will indicate the absence of the viral antibody. The test material, in general, is a serum specimen taken from a patient suspected of suffering from infection with the virus in question. The serum will usually contain antibodies to said virus if the patient is infected with same.

The difference in the degree of hemolysis between control and unknown can be assessed by measuring colorimetrically the extent of hemoglobin tinting of the hemolysate. When RBC are used in high dilutions the released hemoglobin from lysed RBC is allowed to react with an appropriate reagent (added to the hypotonic solution) in order to develop a color which then is read colorimetrically. The latter procedure affords amplification of the tint of the hemolysate. The colorimeter can measure the optical density of the color produced (at 541 nm for hemoglobin, or at other appropriate wave lengths, if reagents for hemoglobin are used), or a filter complimentary to the color produced (by hemoglobin or by its reaction produce after exposure to a reagent) can be placed in the path of a light beam which passes through the tinted hemolysate and is focused so as to excite a photosensitive cell. In this case the generated electrical signal will be proportional to the quantity of light which in turn will be inversely proportional to the degree of hemolysis. A photomultiplier may be required to increase the electrical signal which is registered. It is apparent that detection of an agglutinating factor in the unknown material consists of comparing electrical signals generated by the test sample and corresponding controls, thus providing an end point suitable for automated equipment.

One method of carrying out the method of the present invention is illustrated in FIG. 1a where a test tube is indicated generally by the reference numeral 11, said test tube 11 having therein a hydrophobic liquid layer 12 resting on a layer of hypotonic solution 13 which in turn is resting on a layer 14 of formalin saturated with NaCl. Although the formalin and the hypotonic solution ar miscible, if the formalin is introduced carefully by means of a pipette in the bottom of the test tube, the solutions will stay essentially separate. Of course, any other fixative for RBC may be used instead of formalin. Further, the test may be carried out without use of the hydrophobic liquid layer 12, but test results will not be so sharply differentiated.

Light from a source 16 is collimated by lens 17 into a beam which passes through filter 18 using light at a wavelength strongly absorbed by hemoglobin or by any reagent added to enhance the color produced by hemolysis of RBC. The light beam, after passing through hypotonic layer 13 enters photodetector 19 and the electrical signal therefrom may be amplified, recorded and printed out, as desired.

To carry out a test, RBC are treated with a solution suspected of containing an agglutinating factor and then dropped into the test tube, the RBC first passing through lipid layer 12 and thence through hypotonic solution layer 13 and into fixative layer 14. Lysis takes place only while the RBC are passing through hypotonic solution layer 13. Bubbling of air into the hypotonic solution by means of a small diameter tubing the tip of which is positioned about 1 cm above the fixative results in an even distribution of the released hemoglobin in the hypotonic solution.

Figure 1B:
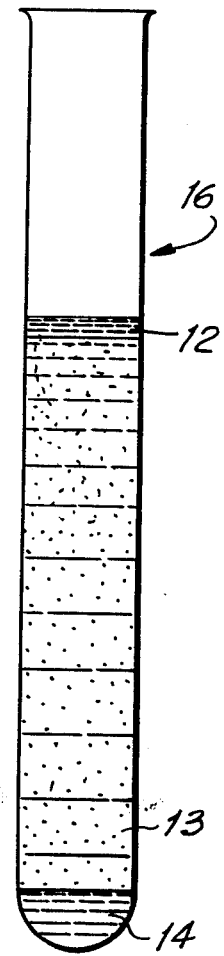

Test tube 11 is indicative of the color when strong lysis occurs and test tube 16 (FIG. 1b) illustrates the situation where only minimal lysis occurs. It should be noted that the dots in FIGS. 1a and 1b indicate color density and not cells.

In general, it is preferable to transfer a portion of the hypotonic solution 13 in which lysis has occurred to a cuvette which is then placed in a colorimeter for determination of the degree of lysis, rather than to carry out the determination in the test tube itself as shown in FIG. 1. Alternatively, the reaction can be carried out in a cuvette which can then be transferred to a colorimeter. These methods will be described with respect to FIGS. 2 and 3. Also, the method of preparation of red blood cells for test will be described in connection with the examples provided below.

Hemolysis is not an "all or none" phenomenon and the presence of agglutinating factors in the test material does not always completely protect the RBC against lysis. Hemolysis may still take place proceeding, however, at a slower rate as compared to that of "unprotected" RBC. In view of the above, it is evident that after a variable period of time depending on the materials used and the conditions of the test, hemolysis and the amount of released hemoglobin will reach a maximum level which then will be indistinguishable from that of the control, assuming that the same number of RBC were present in both control and test mixtures. Consequently it is important that the readings on the degree of hemolysis for both control and test mixtures are obtained after an optimum interval sufficient to allow some hemolysis in the control mixture but not so prolonged as to allow the possibility that the test mixture has reached maximal hemolysis. Prevention of maximal hemolysis can also be accomplished by allowing the RBC to lyse only while sedimenting through a column of hypotonic solution. The RBC, which escaped lysis upon reaching the bottom of the column are either removed or placed in contact with a fixative (e.g. formalin) to prevent further lysis (FIG. 1). The height of the column of the hypotonic solution can be adjusted so as to allow some but not maximal lysis. The contrast of degree of hemolysis between RBC complexes containing the agglutinating factor and corresponding control complexes increases when these complexes are placed in hypotonic solutions (e.g. 0.2–0.4% saline solution) having an osmotic pressure higher than that of distilled water.

In view of the fact that the basic principle described above can be applied in many different ways for detection of a variety of substances, it is not possible to provide examples covering every possible variation in the methodology. Of the three examples which follow, two concern methods which lend themselves for automated blood-typing and cross-matching and the third concerns a method which is suitable for use with kits. They are given to illustrate the practical application of the basic principle using three variations in methodology.

EXAMPLE 1

Determination of Blood Group of Typing Erythrocytes

Reagents:
 Agglutinins (Blood Grouping Sera): Anti-A, anti-B and anti-Rho typing sera were mixed with a double volume of peanut oil (or corn oil) and vigorously shaken for 30–60 seconds. The mixtures were then centrifuged, the lipid phase discarded and the sera (aqueous phase) kept refrigerated until use.
 Known (control) RBC: A-Rh positive and B-Rh negative RBC were washed 3 times with normal saline and the packed cells mixed with 0.9% NaCl solution to form a 10% suspension.
 Unknown blood No. 1: The packed cells were mixed with 0.9% NaCl solution to form a 10% suspension.
 Unknown blood No. 2: Treated as above.
 Hypotonic solution: An 0.27% NaCl solution was prepared, the difference in lysis being at maximum at this concentration.
Procedure:
 (1) A duplicate series of 12 test tubes (6 for controls and 3 for each of the unknown bloods) measuring 13 × 100 mm were consecutively numbered from 1 to 12. (Duplicate series was numbered 1'–12').
 (2) 0.1 ml of the various lipid-treated typing sera and 0.1 ml of the known or unknown RBC were placed in the test tubes in combinations shown in Table 1. The tubes were shaken for 15 seconds and then incubated (at room temperature) for 10 minute.

(3) 5 ml of the saline reagent was added to each tube (by pouring the reagent against the inside wall at the upper end of the tube).

(4) 5 minutes after the addition of the hypotonic saline solution, the optical density (degree of hemoglobin tinting) of the resulting hemolysate in each tube was read by a colorimeter at a wave length of 541 nm.

It should be noted, that, according to the procedure followed in this Example, the agglutinating factor is treated with the hydrophobic substance prior to bringing the serum in contact with RBC.

TABLE I

| Tube No. | Agglutinin | RBC | O.D. at 541 nm tubes 1-12 | tubes 1'-12' | Mean | Hemolysis |
|---|---|---|---|---|---|---|
| 1 and 1' | anti-A | A-Rh neg. | 2.5 | 3.5 | 3.0 | — |
| 2 and 2' | anti-B | A-Rh neg. | 18.5 | 23.0 | 21.0 | + |
| 3 and 3' | anti-Rh | A-Rh neg. | 18.5 | 23.5 | 21.0 | + |
| 4 and 4' | anti-A | B-Rh pos. | 18.0 | 18.0 | 18.0 | + |
| 5 and 5' | anti-B | B-Rh pos. | 3.5 | 3.5 | 3.5 | — |
| 6 and 6' | anti-Rh | B-Rh pos. | 3.5 | 3.5 | 3.5 | — |
| 7 and 7' | anti-A | Unknown 1 | 5.0 | 5.0 | 5.0 | — |
| 8 and 8' | anti-B | Unknown 1 | 23.0 | 22.0 | 22.5 | + |
| 9 and 9' | anti-Rh | Unknown 1 | 4.0 | 3.5 | 4.0 | — |
| 10 and 10' | anti-A | Unknown 2 | 18.0 | 20.0 | 19.0 | + |
| 11 and 11' | anti-B | Unknown 2 | 20.0 | 21.0 | 20.5 | + |
| 12 and 12' | anti-Rh | Unknown 2 | 22.0 | 20.0 | 21.0 | + |

Under conditions of this procedure, complexes of RBC with homologous agglutinin when in contact with the hypotonic solutions release hemoglobin producing an O.D. of 2-5. Complexes of RBC with heterologous agglutinin release hemoglobin producing an O.D. of 17-24. Therefore any O.D. below 7 is considered to correspond to non-hemolysed RBC (agglutination). O.D.'s between 7 and 15 were never encountered except in dilution tests. Assuming they could occur, results with O.D.'s between 7 and 15 should be discarded and the test repeated or other methods applied.

Results and interpretation:

As indicated in the note at the bottom of Table I, an optical density (O.D.) of 15 is considered the minimum reading in accepting results as indicative of hemolysis and an O.D. of 7 is set as the maximum reading in accepting results indicative of non-hemolysis. The control tubes (1–6 and 1'-6') must give O.D.'s within the accepted ranges or the results are not accepted as valid.

In the results shown in Table I, the control tubes (1-6 and 1'-6') gave O.D.'s within the acceptable ranges and therefore the results are accepted as valid The RBC of the unknown blood sample 1 mixed with anit-B serum were hemolysed (not agglutinated). The RBC mixed with anti-A and anti-Rh sera were not hemolysed (agglutinated). Therefore these RBC having agglutininogens A and Rh but lacking agglutininogen B and A-Rh positive.

The RBC of the unknown blood sample 2 were hemolysed with anit-A, anti-B and anti-Rh sera. Therefore these RBC, lacking agglutininogens A, B and Rh, are type O-Rh negative.

The Rh serum used in this example was of the anti-Rho type. This is the type generally used, but, as is evident, any of the other Rh anti-sera could have been used in order to detect other specific Rh factors.

A modification of this procedure to take account of possible variations in the hemoglobin content among patients can readily be made. A sample of RBC from a specific patient is hemolysed without any "protection" whatsoever and the optical density measured. The test results by the standard procedure are then presented relative to that obtained with the unprotected RBC.

The steps in the above procedure were described as being carried out manually. However they can also be carried out in automatic apparatus as shown in FIG. 2. An automatically-sequenced sampler 21 is shown as containing sample tubes 22 each of which contains red blood cells which have been washed with normal saline and then suspended in normal saline solution. A sample tube from which a sample is being taken is represented schematically by the reference numeral 23. An automatic pipetting device 24 takes a representative sample of RBC in normal saline and transfers the sample to a lysing tube 26 which is supported and automatically transferred along tube drive 27 by drive means which are not shown.

A reagent manifold is indicated generally by reference numeral 28. In the apparatus as shown in FIG. 2, the reagent manifold 28 contains anti-A, anti-B and anti-Rho sera as well as hypotonic saline solution. The manifold, if desired, may also contain the anti-Coomb's, M and N sera as well as anti-sera for other Rh factors. Each of the sera has been shaken with a lipid, i.e., a hydrophobic substance, preferred hydrophobic substances being peanut oil and corn oil, and separated therefrom. To type the RBC in sample tube 23, three lysing tubes 26 are needed. Reagent-delivery means 29 transfers the three sera to three lysing tubes 26, respectively. Each of the three tubes 26 now contains one of the sera and RBC in normal saline. Each lysing tube is shaken by vibrator 31. The tubes are then moved along the drive to position 32, the spacing between positions 32 and 33 being correlated with the rate at which the tubes are moved to provide the appropriate incubation period between the RBC and the serum. At position 32, hypotonic solution is added by reagent delivery means 29 to the lysing tube and lysis begins. Again, the distance between position 32 and 34, in combination with the rate at which the tubes are moved, provides a standardized lysing period. At position 34 feeder 36 withdraws a portion of the solution from lysing tube 26 and transfers it to a cuvette (not shown) in colorimeter 37. The cuvette is cleaned or replaced between samples. Optionally, the electrical signal produced by colorimeter 37 can be recorded by recorder 38, or can be transferred to a computer 39 and display means such as a printer or CRT 41.

As is obvious, information, indicated by the arrow 42, must be transferred between sampler 21 and colorimeter 37 in order to correlate the results measured in colorimeter 37 with the specific test tube 23 from which the specimen to be measured was originally taken.

In another embodiment of the invention cuvettes are used in the tube drive as lysing tubes, in which case feeder 36 is not needed. Instead, the tube drive is so constructed that it transfers the cuvettes directly to the colorimeter 37. It is necessary that control speciments be run periodically as a basis for comparison and judging the lysis for the particular types of cells and sera in use. The same embodiment of the apparatus can be used for typing sera by placing the lipid-treated sera in the sampler 21 and known RBC suspensions in the manifold 28. Also, the sera can be used without pretreatment with lipid.

EXAMPLE 2

Determination of Blood Group by Typing Sera

Reagents:
   Agglutinins (Blood Grouping Sera): Anti-A, anti-B and anti-Rho typing sera were kept refrigerated until use.
   Unknown Serum 3
   Unknown Serum 4
   Erythrocytes: A-Rh negative, B-Rh negative and O-Rh positive RBC were washed 3 times with normal saline and the packed cells mixed with 0.9% NaCl solution to form a 10% suspension.
   Formalin-NaCl Solution: 37% formaldehyde solution was saturated with sodium chloride.
   Deionized water
   Corn Oil Procedure:
   (1) A duplicate series of 12 test tubes (6 for controls and 3 for each unknown serum) measuring 12 × 100 mm were consecutively numbered from 1 to 12 (duplicate series was numbered 1'-12').
   (2) 5 ml of deionized water were placed in each of the above tubes. The height of the water column was about 6cm.
   (3) 1 ml of the formalin-NaCl solution was gently deposited at the bottom of each of the above tubes so that two separate phases were formed.
   (4) 2 ml of corn oil was laid on the surface of the water phase of each of the above tubes. Now each tube contained 3 distinct phases, oil phase on top, a formalin-NaCl phase at the bottom and a water phase in between.
   (5) In another duplicate series of 12 test tubes, 0.1 ml of the various RBC and 0.1 ml of the known agglutinins and the unknown sera were mixed in combinations shown in Table II.
   (6) The mixtures were shaken for 15 seconds and then deposited into the oil phase of the corresponding tubes described in paragraphs 1-4.
   (7) After varying periods of time the RBC-serum mixtures passed from the oil phase into the water phase. Such hemolysis as occurred took place while the RBC were travelling by gravity through the water phase. The RBC which escaped hemolysis, on reaching the formalin-NaCl phase at the bottom of the tubes were fixed so that any further hemolysis was prevented. Five minutes after the RBC-serum mixtures entered the water phase the O.D.'s of the hemolysates (water phase) were read in a colorimeter at 541 nm.

TABLE II

| Tube No. | Agglutinin | RBC | O.D. at 541 tubes 1-12 | O.D. at 541 tubes 1'-12' | Mean | Hemolysis |
|---|---|---|---|---|---|---|
| 1 and 1' | Anti-A | A-Rh neg. | 4.5 | 5.5 | 4.5 | − |
| 2 and 2' | Anti-A | B-Rh neg. | 23.5 | 22.5 | 23.0 | + |
| 3 and 3' | Anti-B | A-Rh neg. | 24.5 | 29.5 | 27.0 | + |
| 4 and 4' | Anti-B | B-Rh neg. | 7.0 | 5.5 | 6.0 | − |
| 5 and 5' | Anti-Rh | O-Rh neg. | 19.0 | 20.0 | 19.5 | + |
| 6 and 6' | Anti-Rh | O-Rh pos. | 3.0 | 4.0 | 3.5 | − |
| 7 and 7' | Unknown serum 3 | A-Rh neg. | 2.5 | 3.5 | 3.0 | − |
| 8 and 8' | Unknown serum 3 | B-Rh neg. | 22.0 | 18.0 | 20.0 | + |
| 9 and 9' | Unknown serum 3 | O-Rh pos. | 3.0 | 3.0 | 3.0 | − |
| 10 and 10' | Unknown serum 4 | A-Rh neg. | 18.5 | 23.0 | 21.0 | + |
| 11 and 11' | Unknown serum 4 | B-Rh neg. | 3.5 | 3.5 | 3.5 | − |
| 12 and 12' | Unknown serum 4 | O-Rh pos. | 20.0 | 22.0 | 21.0 | + |

Results and Interpretation:

Table II shows that the mixtures of unknown serum 3 with A-Rh neg. RBC and with O-Rh pos. RBC were not hemolysed (the RBC were agglutinated), while the mixture with B-Rh neg. RBC was hemolysed (the RBC were not agglutinated). Serum 3, therefore, contained anti-A and anti-Rh but not anti-B agglutinins. This serum, therefore, was derived from a type B blood which contains anti-Rh antibodies.

The mixture of unknown serum 4 with B-Rh neg. RBC was not hemolysed while those with A-Rh neg. and with O-Rh pos. RBC were hemolysed. Serum 4, therefore contained anti-B but not anti-A or anti-Rh agglutinins. This serum, therefore, was derived from a type A blood which contains no anti-Rh antibodies.

The results of this test were accepted as valid, since, as Table II indicates, the control mixtures of RBC and sera which were expected to agglutinate and therefore resist hemolysis gave an O.D. of 3 to 6 (within acceptable range) and those which were expected not to agglutinate and therefore hemolyse gave O.D.'s between 19.5 and 27 which were again within acceptable limits.

Figure 3:
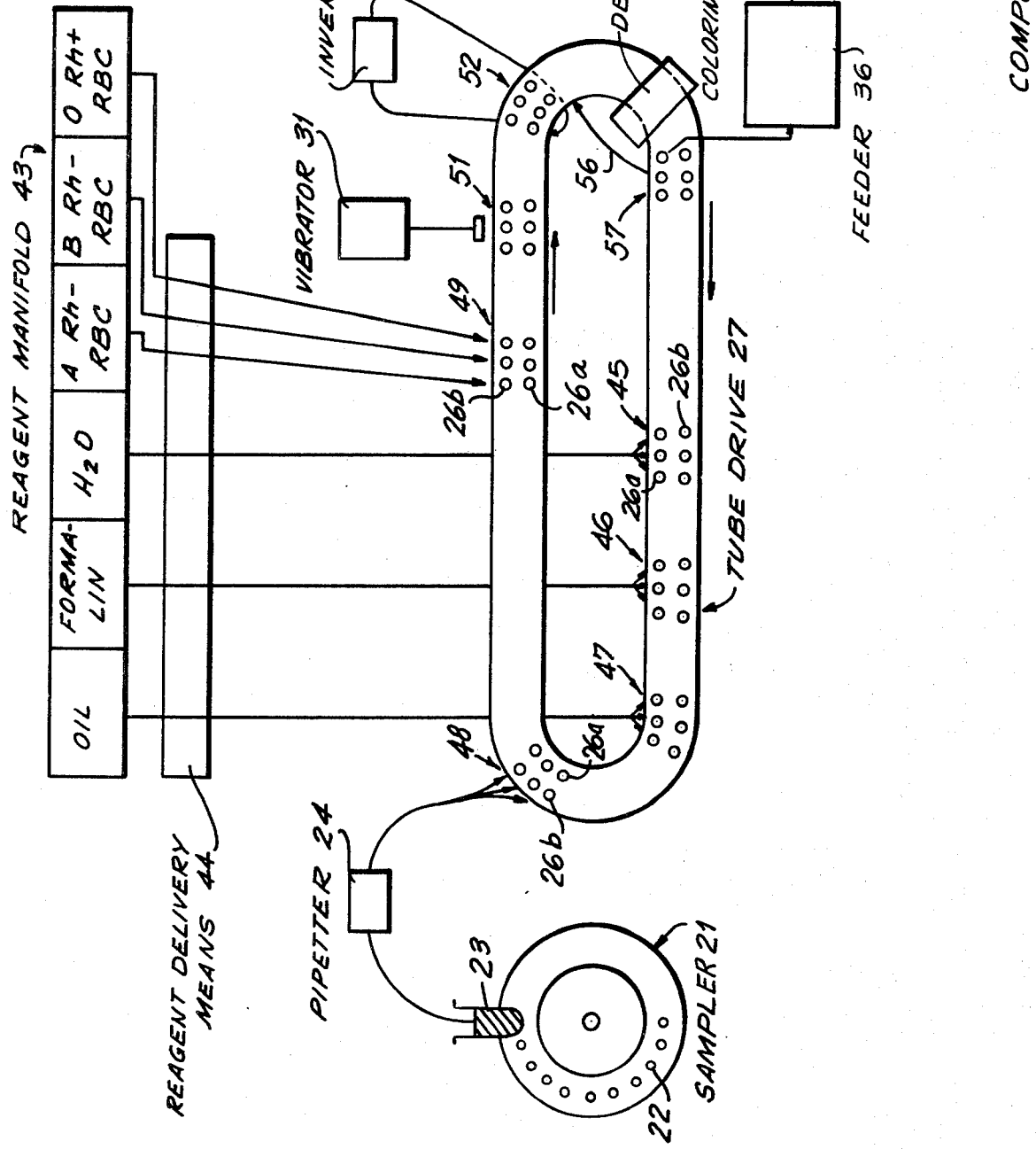
FIG. 3 is a second embodiment of the apparatus in accordance with the present invention.

Apparatus for carrying out the test as described in Example 2 is shown in FIG. 3. Automatically-driven sampler 21 moves tubes 22 containing sera to be typed to position 23 at which position samples are automatically removed from tubes 22 by automatic pipetter 24.

Lysing-tube drive 27 moves groups of lysing tubes in groups of 6. Each group of 6 is divided into two subgroups of 3, the two subgroups of 3 being indicated by the reference numerals 26a and 26b.

Reagent manifold 43 has therein compartments or vessels containing a hydrophobic substance or lipid indicated by the term "oil", a fixative indicated as "formalin" and water, as well as types A, Rh negative; type B, Rh negative; and type O, Rh positive blood cells. At position 45 the three lysing tubes of subgroup 26a each receive water. At position 46 a layer of formalin is pipetted to the bottom of each of the lysing tubes 26a, and at position 47 a layer of oil is deposited on top of the layer of water. This last step can be omitted, if desired, but contrast is decreased.

When the groups of 6 lysing tubes reach position 48 automatic pipetter 24 places a specimen of the serum from sample tube 23 in each of the three tubes 26b. The group of 6 then moves along to position 49 at which point type A, Rh negative RBC are added to one of the tubes 26b, type B, Rh negative RBC are added to the second of these tubes and type 0, Rh positive RBC are added to the third of these tubes. When the group of 6 reaches position 51, vibrator 31 shakes up the lysing tubes 26b, thereby making good contact between the red blood cells in each of the three tubes and the serum specimen in each tube.

The lysing tubes are then carried along tube drive 27 until they reach position 52, at which point inverter 53 transfers a serum-RBC specimen from a tube of the subgroup 26b to a corresponding tube of the subgroup 26a, the addition being made gently so that the red blood cells are deposited in the oil layer near the top of the tube.

In general, the treated red blood cells will leave the oil layer fairly quickly and descend through the water layer, lysing during the time of transit through the water layer. However, there may be a substantial interval between the time when the red blood cells are placed in the oil layer and the time when the cells enter the water layer. Since lysing cannot take place before the cells enter the water layer, it is necessary to determine whether the transfer from the oil layer to the water layer has taken place before attempting to measure the degree of lysis. Accordingly, detector 54 is positioned for determining whether the drop of serum containing red blood cells has left the oil layer and entered the water layer. One method of detecting this transfer is by positioning a light beam and photodetector tube in relation to tube drive 27 in such a manner that the presence of a water droplet in the oil layer will deflect the beam. Detector 54 can also be set up so that it detects red blood cells falling through the water layer as a means of determining that the red blood cells have entered the water layer. In the event that detector 54 establishes that the RBC in any particular lysing tube have not entered the water layer as yet, the tube is diverted from its normal path and recycles as indicated by the arrow labelled with the reference numeral 56. If necessary, the operation can be repeated until such time as the RBC enter and fall through the water layer.

When lysing tubes 26a reach position 57, feeder 36 transfers the tubes to colorimeter 37 where the degree of lysis is determined by means of the depth of color. The output from the colorimeter is transferred to recorder 38, or optionally to computer 39 and then to display means 41.

When the reading by colorimeter 37 is complete, the individual tubes 26a can be discarded. Alternatively, specimens from the water layer can be taken by feeder 36 and transferred to a cuvette in colorimeter 37, the cuvette being washed, cleaned and dried between successive readings of successive tubes. In general where the reading is carried out directly on the lysing tube there may be an optimum height or level in the water layer at which the degree of contrast with respect to a control tube is maximum. Preferably, readings are taken at this height. Needless to say, control tubes are put through the system to make certain that the system is operating properly and to provide a standard against which to compare the degree of lysis resulting from treatment of a specimen. A control tube is one in which the reaction to be carried out is one between a known agglutinin type and a known RBC type.

The same embodiment of the apparatus can be used for typing RBC by placing the RBC in sampler 21 and typing sera in manifold 43.

EXAMPLE 3

Detection of Antiviral Antibody

Reagents:
Influenza Type B Virus (Hong Kong strain) Grown in Amniotic Sac of Chick Embryo: Virus-containing amniotic fluid was diluted 1:2 with normal saline, mixed with a double volume of corn oil, shaken, centrifuged and the water phase refrigerated until use.

Antiviral antibody: Serum containing antibodies against the above-mentioned influenza virus was diluted 1:2 with normal saline.

Control Serum: (Serum containing no antibody against the above-mentioned influenza virus.) Human serum from AB-type blood containing no isoagglutinins, Rh antibodies or Coomb's antibodies was diluted 1:2 with normal saline.

Erythrocytes: Type O-Rh negative, Coomb's negative erythrocytes were washed 3 times with normal saline and the packed cells mixed with normal saline to form a 0.5% suspension.

Hypotonic-hemoglobin reagent: 1 tablet of Hematest (Ames Co.) was placed in 100 ml of 0.27% NaCl solution. The tablet was crushed and dissolved to form a saturated solution. The solution was centrifuged and the supernatant used as the hypotonic hemoglobin reagent.

Normal saline: 0.9% NaCl solution.

Procedure:
(1) In a duplicate series of 5 test tubes (13×100 mm) numbered 1–5 and 1′–5′ influenza virus, antiviral antibody, control serum and normal saline were added in volumes shown in Table III.
(2) The mixtures were shaken and incubated at room temperature for 20 minutes.
(3) 0.1 ml of the erythrocyte suspension was added to all tubes.
(4) The mixture was incubated for 15 minutes at room temperature.
(5) 5 ml of the hypotonic-hemoglobin reagent was gently added to all tubes. (The reagent was poured against the inner wall of the tubes).
(6) The intensity of the developed blue color was visually compared between tubes 1 and 2, 1 and 3, and 4 and 5.

TABLE III

| Tube No. | B-Virus | Viral Antibody | Control Serum | Saline |
|---|---|---|---|---|
| 1 and 1′ | 0 | 0 | 0 | 0.2 ml |
| 2 and 2′ | 0 | 0 | 0.2 ml | 0 |
| 3 and 3′ | 0 | 0.2 ml | 0 | 0 |
| 4 and 4′ | 0.1 ml | 0 | 0.1 ml | 0 |
| 5 and 5′ | 0.1 ml | 0.1 ml | 0 | 0 |

Results and Interpretation:

A blue color of approximately the same intensity developed in tubes 1, 2 and 3. The blue color was the result of a reaction between the hypotonic-hemoglobin reagent and the hemoglobin released by the RBC in the hypotonic solution. The fact that the intensities were approximately equal indicates that the control serum as well as the serum containing viral antibodies did not protect the RBC against hemolysis. In tube 5, the intensity of the blue color was greater than in tube 4. This indicates that the RBC mixed with viral antibodies and virus were hemolysed to a greater extent than RBC mixed with control serum and virus.

The procedure for detection of antiviral antibodies is particularly suitable for adaptation to kit form, though, as is evident, the reagents for any of the examples or methods described above could be supplied in kit form. With respect to the method of the present invention as described in Example 3, the kit may contain a vial holding a virus such as, for instance, influenza-type B, the solution containing the virus having already been treated with a lipid, a vial with a control serum, said control serum being known not to contain antibodies against the virus under test, a vial with a 0.27% NaCl solution containing a reagent which reacts with hemoglobin to produce a color, a vial with O-Rh negative, Coomb's negative RBC (0.5% suspension in normal saline) four droppers suitable for delivering 0.1 ml volumes, and 4 test tubes. The kit must be refrigerated for storage and, preferably, should be marked with an expiration date. To use the kit, 0.1 ml of virus is added to tubes 1 and 2 of the four test tubes, 0.1 ml of control serum is added to tube 1, and 0.1 ml of the patient's serum to tubes 2 and 3, the tubes are shaken and allowed to stand for 20 minutes. At the end of this period, 0.1 ml of RBC suspension is added to all four test tubes and after 15 minutes incubation, 5 ml of the hypotonic solution is added to all four test tubes and the developed colors are compared. If the intensity of the color in tubes 3 and 4 is approximately the same, and the intensity in tube 2 is higher than in tube 1, then the test will be considered positive, that is, antibodies against influenza type B virus are present. If the intensity in tube 3 is lower than in tube 4, the results should be discarded. False positive results may be caused by cross-reacting antibodies. False negative results may be due to antiviral antibodies of insufficient titres.

As aforenoted, the various tests described herein can be carried out without the use of a lipid, or hydrophobic substance. However, the difference in the reliability of the test can be seen from the fact that clumped RBC which have been treated with lipid give an O.D. range of 2-6 and unclumped RBC give an O.D. range of 17-30, a difference which is easy to distinguish, whereas clumped RBC which have not been lipid-treated give an O.D. range of 6-15.

It will thus be seen that the objects set forth above, among those made apparent from the preceding description, are efficiently attained and, since certain changes may be made in carrying out the above method and in the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method for blood-typing, for identifying viruses and other red blood cell-agglutinating substances including factors originating in tumors, and for detecting the presence of and identifying antibodies in sera, comprising the steps of (a) treating red blood cells with a test solution suspected of containing therein an agglutinating factor for said red blood cells, or of containing a complex of an agglutinating factor with an antibody thereto, (b) bringing said treated red blood cells into contact with a hypotonic solution under conditions such as to cause strong lysis in untreated red blood cells, and (c) noting by means of color changes the extent of lysis, a degree of lysis comparable to that of red blood cells treated with a serum known to lack a corresponding agglutinating factor indicating the absence of said suspected agglutinating factor, or the presence of a complex of said agglutinating factor with the antibody thereto, and a substantially reduced degree of lysis indicating the presence of said suspected agglutinating factor uncomplexed with an antibody.

2. The method as defined in claim 1, further comprising the step of treating said red blood cells with a hydrophobic substance prior to bringing said red blood cells into contact with said hypotonic solution.

3. The method as defined in claim 2, wherein said red blood cells are treated with said hydrophobic substance by treating said test solution with said hydrophobic substance and subsequently bringing said test solution into contact with said red blood cells.

4. The method as defined in claim 2, wherein said red blood cells are treated with said hydrophobic substance by treating said agglutinating factor in said test solution with said hydrophobic substance and subsequently bringing said test solution into contact with said red blood cells.

5. The method as defined in claim 2, wherein said red blood cells are treated with said hydrophobic substance by treating said red blood cells with said test solution and subsequently with said hydrophobic substance.

6. The method as defined in claim 2, wherein said hydrophobic substance is adsorbable by said suspected agglutinating factor but not said red blood cells.

7. The method as defined in claim 2, wherein said hydrophobic substance is a lipid.

8. The method as defined in claim 2, wherein said hydrophobic substance is a member of the group consisting of saturated and unsaturated fats and oils.

9. The method as defined in claim 8, wherein said hydrophobic substance is a member of the group consisting of edible oils and fats.

10. The method as defined in claim 8, wherein said hydrophobic substance is a member of the group consisting of peanut oil and corn oil.

11. The method as defined in claim 8, wherein said hydrophobic substance is adsorbable by said agglutinating factor and not by said red blood cells.

12. The method as defined in claim 2, wherein red blood cells of unknown type are treated with a hydrophobic substance and with at least one of blood-grouping sera containing respectively anti-A, anti-B, anti-Rh, anti-M, anti-N and anti-Coomb's agglutinating factors as a means of typing said red blood cells.

13. The method as defined in claim 12, wherein said blood-grouping sera are treated with said hydrophobic substance prior to treating said red blood cells with said blood-grouping sera.

14. The method as defined in claim 12, wherein said red blood cells are treated with said blood-grouping sera prior to treating said blood cells with said hydrophobic substance.

15. The method as defined in claim 1, wherein said treatment is carried out automatically.

16. The method as defined in claim 12, wherein said treatment is carried out automatically.

17. The method as defined in claim 1, wherein said step of noting the degree of lysis is carried out automatically.

18. The method as defined in claim 12, wherein said step of noting the degree of lysis is carried out automatically.

19. The method as defined in claim 1, wherein said a serum of unknown type is treated with red blood cells of at least one of types A, B, M and N and Rh positive, and Coomb's positive as a means of typing said serum.

20. The method as defined in claim 19, further comprising the step of treating said serum of unknown type with a hydrophobic substance prior to bringing said red blood cells into contact with said hypotonic solution.

21. The method as defined in claim 19, wherein said treatment is carried out automatically.

22. The method as defined in claim 19, wherein said step of noting the degree of lysis is carried out automatically.

23. The method as defined in claim 2, wherein said test solution is prepated by mixing a biological fluid suspected of containing a specific virus and serum known to contain the antibody to said virus, and said red blood cells are type O, Rh negative.

24. The method as defined in claim 23, wherein said treatment is carried out automatically.

25. The method as defined in claim 23, wherein said step of noting the degree of lysis is carried out automatically.

26. The method as defined in claim 2, wherein said test solution is prepared by mixing a biological fluid containing a specific virus and serum from a patient suspected of containing antibodies to said virus, and said red blood cells are type O, Rh negative.

27. The method as defined in claim 26, wherein said treatment is carried out automatically.

28. The method as defined in claim 26, wherein said step of noting the degree of lysis is carried out automatically.

29. The method as defined in claim 2, wherein said hypotonic solution is an aqueous solution of NaCl at a concentration between about 0.2% and 0.4%.

30. The method as defined in claim 29, wherein the concentration of said solution is about 0.27%.

31. The method as defined in claim 2, wherein said red blood cells are first treated with said test solution and then introduced into a vessel containing a layer of red blood cell fixative on the bottom thereof, a layer of said hypotonic solution over said layer of fixative and a layer of said hydrophobic substance over said layer of hypotonic solution, said serum being introduced into said vessel under conditions such that said red blood cells fall through said layers, whereby lysis takes place only during the time of transit of said cells through said hypotonic solution layer, said cells being fixed on entering said fixative layer.

32. The method as defined in claim 2, wherein said test is repeated with said test solution at at least one lower concentration as a means of semi-quantitation of said suspected agglutinating factor by determining the lowest concentration at which the degree of lysis is comparable to that of red blood cells treated with a serum known to lack a corresponding agglutinating factor.

33. The method as defined in claim 1, further comprising the step of adding to said hypotonic solution a reagent known to enhance the intensity of the color, thereby increasing the precision with which the extent of lysis can be determined.

34. A fluid comprising a member selected from the group consisting of anti-A agglutinin, anti-B agglutinin, anti-Rh agglutinin, anti-human γ-globulin and viruses capable of agglutinating red blood cells, and a hydrophobic substance combined with said member said hydrophobic substance being present in sufficient quantity to substantially reduce the rate of lysis which would otherwise occur on adding corresponding red blood cells to said fluid and combining the resultant produce with hypotonic solution.

35. Apparatus for automatic blood-typing, crossmatching, identifying viruses, detecting the presence of and identifying antibodies in sera, and detecting agglutinating factors derived from tumors, comprising (a) containers for holding washed red blood cells, hereinafter referred to as "RBC", suspended in saline solution;

(b) first conveyor means for transporting said containers in preparation for removing samples from said containers;

(c) lysing tubes for holding test reagents and RBC samples taken from said containers;

(d) second conveyor means for transporting a plurality of said lysing tubes;

(e) reagent manifold for holding and supplying at least one agglutination reagent hereinafter termed "AR", and hypotonic solution to each of said lysing tubes, the term "hypotonic solution" being taken to include water;

(f) automatically sequenced sampler for transferring samples of RBC from each of said containers to a number of lysing tubes equal to the number of AR to be used in typing said RBC;

(g) first delivery means for supplying each AR individually to a corresponding number of lysing tubes;

(h) mixing means including shaker or vibrator means positioned for mixing the contents of said lysing tubes essentially immediately and for a controlled period of time subsequent to addition of said AR;

(i) second delivery means for adding hypotonic solution to the contents of said lysing tubes subsequent to addition of AR, said first delivery means, mixing means and second delivery means being spaced apart along said second conveyor means for providing a controlled incubation period;

(j) colorimeter means for determining quantitatively the degree of osmotic lysis of said RBC in said lysing tubes, said colorimeter means being spaced apart from said second delivery means; and (k) drive means for driving said second conveyor means at a rate such that, in combination with said spacing between said second delivery means and said colorimeter, a suitable fixed time interval is provided for osmotic lysis to proceed to an extent such as to make it possible to determine relative rates of lysis in different samples.

36. The apparatus as defined in claim 35, wherein said apparatus further comprises means for treating said red blood cells with a hydrophobic substance prior to bringing same into contact with said hypotonic solution.

37. The apparatus as defined in claim 35, further comprising automatic means for noting said degree of lysis, for determining the presence of specific agglutinating factors from said degree of lysis and for determining the blood group corresponding to the determined agglutinating factors when said apparatus is used for blood typing.

38. The apparatus as defined in claim 35, wherein said AR is lipid-treated.

39. The apparatus as defined in claim 35, wherein said lysing tubes are cuvettes suitable for use with said colorimeter.

40. The apparatus as defined in claim 35, further comprising cuvettes for use with said colorimeter and automatic feeder means for transferring specimens of solution from said lysing tubes to said cuvettes.

41. Apparatus for automatically detecting and determining agglutination factors in a fluid, including the typing of sera, said agglutination factors hereinafter termed "AFs", comprising:
  (a) containers for holding specimen fluids to be tested for the presence of specific AFs;
  (b) first conveyor means for transporting said containers for convenience in removing samples from said containers;
  (c) a plurality of test tubes divided into groups, the number of test tubes in each group corresponding to the number of types of red blood cells, hereinafter termed "RBC" to be used as test reagents;
  (d) lysing tubes divided into groups, there being a lysing tube corresponding to each test tube;
  (e) second conveyor means for transporting said test tubes and lysing tubes;
  (f) first reagent manifold for holding and addition means for supplying liquid lipid, fixative, and hypotonic solution to each of said lysing tubes in such manner that a layer of fixative rests at the bottom of said tube, a layer of hypotonic solution rests on said layer of fixative and a layer of lipid rests on said layer of hypotonic solution;
  (g) automatically sequenced sampler for transferring samples of serum from a container to all of the test tubes in a group;
  (h) second reagent manifold and second addition means for supplying a different type of RBC to each of the test tubes in said group;
  (i) mixing means for mixing the serum sample and RBC in each of the test tubes in said group;
  (j) transfer means for transferring the contents of each of said test tubes in a group to said lipid layer in a corresponding lysing tube for dropwise descent, by gravity, of said test tube contents through said lipid layer and said layer of hypotonic solution and into said fixative layer; and
  (k) colorimeter means positioned for passing a beam of light through said layer of hypotonic solution for determining quantitatively the degree of lysis of said RBC in falling through said layer of hypotonic solution to said fixative.

42. The apparatus as defined in claim 41, further comprising:
  (l) detector means for determining prior to arrival of a lysis tube at said colorimeter means whether all of the RBC in same have fallen through said hypotonic solution; and
  (m) recycling means operatively connected to said detector means for recycling any lysis tube containing RBC above said hypotonic solution layer to said detector means until all RBC have passed through said hypotonic solution and then transferring said lysis tube to said colorimeter means.

43. The apparatus as defined in claim 41, further comprising automatic means for noting said degree of lysis, for determining the presence of specific agglutinating factors from said degree of lysis and for determining the blood group corresponding to the determined agglutinating factors when said apparatus is used for blood typing.

44. A composition for detecting the presence of a specific viral antibody in a biological specimen, said composition comprising a virus corresponding to said antibody, a fluid suitable for suspending said virus, and a lipid in an amount such as is held by said fluid and said virus following agitation with said lipid and physical separation therefrom, said composition being useful for determining the presence of said specific antibodies by the degree of osmotic hemolysis of red blood cells when brought in contact therewith and with hypotonic solution.

* * * * *